United States Patent [19]
Salzman et al.

[11] Patent Number: 5,423,320
[45] Date of Patent: Jun. 13, 1995

[54] AIR TONOMETRY METHOD AND APPARATUS FOR MEASURING INTRALUMINAL GASTROINTESTINAL $PCO_2$ AND $PO_2$

[75] Inventors: Andrew L. Salzman, Wayland; Mitchell P. Fink, Dover; Jeffrey B. Kane, Boston, all of Mass.

[73] Assignee: Argus Critical Care, Inc., Boston, Mass.

[21] Appl. No.: 49,549

[22] Filed: Apr. 20, 1993

[51] Int. Cl.$^6$ .............................................. A61B 5/00
[52] U.S. Cl. .................................... 128/664; 128/634; 128/637
[58] Field of Search ............................... 128/633–635, 128/637, 664–665, 632

[56] References Cited

U.S. PATENT DOCUMENTS

| | | | |
|---|---|---|---|
| 4,016,863 | 4/1977 | Brantigan . | |
| 4,187,856 | 2/1980 | Hall et al. | 128/635 |
| 4,221,567 | 9/1980 | Clark et al. | 128/635 X |
| 4,301,809 | 11/1981 | Pinchak | 128/695 |
| 4,381,011 | 4/1983 | Somers, 3rd | 128/635 |
| 4,424,276 | 1/1984 | Clark et al. | 436/50 |
| 4,567,748 | 2/1986 | Klass et al. | 73/1 G |
| 4,643,192 | 2/1987 | Fiddian-Green | 128/632 |
| 4,803,992 | 2/1989 | Lemelson | 128/634 |
| 4,854,321 | 8/1989 | Boiarski | 128/634 |
| 4,901,727 | 2/1990 | Goodwin | 128/632 |
| 4,949,724 | 8/1990 | Pieter et al. | 128/713 |
| 4,996,990 | 3/1991 | Hideshima | 128/648 |
| 5,020,537 | 6/1991 | Gunther | 128/634 |
| 5,031,623 | 7/1991 | Kohayakawa et al. | 128/648 |
| 5,115,811 | 5/1992 | Hartlaub et al. | 128/634 |
| 5,176,882 | 1/1992 | Gray et al. | 422/82 |
| 5,186,172 | 2/1993 | Fiddian-Green | 128/632 |
| 5,193,544 | 3/1993 | Jaffe | 128/634 |

OTHER PUBLICATIONS

Bass et al., "Intraluminal pCO2: A Reliable Indicator of Intestinal Ischemia," Journal of Surgical Research, vol. 39, pp. 351–360 (1989).
Bullock et al., "A Rapid Scanning Spectrometer for Oscillographic Presentation in the Near Infrared," J. Opt. Soc. Am., vol. 40, No. 9, pp. 608–615 (1950).
Clark et al., "Monitor and Control of Blood and Tissue Oxygen Tension," Trans. Am. Soc. Artif. Intern. Organs, vol. 2, pp. 41–48 (1956).
Kohama et al., "Continuous Monitoring of Arterial and Tissue pCO2 With Sensors Based on the pH-ISFET," Crit. Care-Med., vol. 12, p. 940 (1984).
Kurland et al., "Diagnostic Tests for Intestinal Ischemia," Surg. Clin. North Am., vol. 72, No. 1, pp. 85–101 (1992) Abstract Only.
Larsen et al., "Characterization of the Silicone Tonometer Using a Membrane–Covered Transcutaneous Electrode," Scand. J. Clin. Lab Invest, vol. 49, pp. 513–519 (1989).
Lubbers et al., "Quantitative Fluorescence Photometry with Biological Fluids and Gasses," Adv. Exp. Med. Biol., vol. 75, pp. 65–69 (1976).
Pauling et al., "An Instrument for Determining the Partial Pressure of Oxygen in a Gas," Science, vol. 103, p. 338.
Schlichting et al., "[Indirect Measurement of Intramucosal pH in the Gastrointestinal Tract Using a Tonometer. A Useful Marker of Tissue Oxygenation in Critically Ill Patients]," Tidsskr Nor Laegeforen, vol. 112, No. 16, pp. 2096–2099 (1992) Abstract Only.

(List continued on next page.)

*Primary Examiner*—Angela D. Sykes
*Attorney, Agent, or Firm*—Lappin & Kusmer

[57] ABSTRACT

A method and apparatus for measuring or monitoring $pCO_2$, and optionally $pO_2$, on a real-time basis, in the stomach or the intestine using air tonometry. The intraluminal measurements are made using a catheter having a $CO_2$ sensor, and optionally a $pO_2$ sensor, at its tip for in situ measurements, or by circulating a fixed amount of air through the catheter with measurement occurring at the proximal end of the catheter. Instrumentation supporting the sensor may be adapted for location within a patient or external to a patient.

16 Claims, 4 Drawing Sheets

OTHER PUBLICATIONS

Seitz, "Chemical Sensors Based on Fiber Optics," Analytical Chemistry, vol. 56, No. 1, pp. 16A–34A (1984).

Severinghaus et al., "Electodes for Blood pO2 and pCO2 Determination," J. Appl. Physiol, vol. 13, pp. 515–520 (1958).

Stow et al., "Rapid Measurement of the Tension of Carbon Dioxide in Blood," Arch. Phys. Med. Rehabil. vol. 38, pp. 650–656, (1954).

Ueda, "[Clinical Evaluation of Artificial Tonometry for Noninvasive, Continuous Blood Pressure Monitoring During Anesthesial]," Hokkaido Igaku Zasshi, vol. 66, No. 6, pp. 805–817 (1991) Abstract Only.

Vurek et al., "A Fiber Optic pCO2 Sensor," Ann. Biomed. Eng., vol. 11, pp. 499–510 (1984).

AIR TONOMETRY METHOD AND APPARATUS FOR MEASURING INTRALUMINAL GASTROINTESTINAL PCO2 AND PO2

FIELD OF THE INVENTION

The invention is in the field of air tonometry and more particularly relates to apparatus and methods for measuring the partial pressure of carbon dioxide ($pCO_2$) and optionally oxygen ($pO_2$) in gastrointestinal lumen.

BACKGROUND OF THE DISCLOSURE

There currently is substantial interest in tonometric estimation of gastrointestinal intramucosal pH ($pH_i$) as a means for monitoring mesenteric perfusion in critically ill patients. There are two reasons for this: First, alterations in mesenteric perfusion have been associated with derangements in gut barrier function. It has been hypothesized that such derangements might permit the systemic absorption of intact microbes or microbial products into mesenteric lymphatics and the portal venous system, thereby triggering or sustaining the release of pro-inflammatory mediators implicated in the pathogenesis of the multiple organ dysfunction syndrome. Second, studies suggest that blood flow is diverted away from the splanchnic bed in animals subjected to hemorrhage, sepsis, sterile peritonitis, or heart failure. Thus, gastrointestinal $pH_i$ may be able to serve as a sentinel marker of tissue hypoperfusion in various shock states.

Tonometric estimation of mucosal gas tensions has been performed in the urinary bladder and gallbladder. This concept was extended to the gastrointestinal tract when it was observed that the partial pressure of $CO_2$ in the mucosa could be estimated by placing liquid in an isolated bowel segment and allowing adequate time for equilibration with tissue $CO_2$. The application of tonometry as a practical means for monitoring patients has been developed, based on the observation that saline in a permeable silicone balloon equilibrates with tissue $pCO_2$. It has been proposed that tonometry be used to indirectly estimate $pH_i$ in the stomach or colon by inserting the tonometrically measured $pCO_2$ ($TpCO_2$) into a modified Henderson-Hasselbach equation, using the assumption that intracellular and arterial ($HCO_3$) are equal, and, then backcalculating pH. The notion that tonometry could be used to estimate $pH_i$ has been validated by showing the qualitative agreement between values for this parameter obtained by direct measurement with those simultaneously made using the prior art tonometric methods. Further improvement in the accuracy of gastric tonometry as a clinical tool resulted from the observation that intraluminal $CO_2$ production from the combining of gastric acid and secreted bicarbonate could be obviated by pretreatment with $H_2$ antagonists. Other techniques to measure splanchnic $pCO_2$ have included mass spectrometry of $pCO_2$ dissolved in intraluminal fluid and Severinghaus electrode analysis of gastric fluid aspirates, obtained 30 minutes after installation of 30 mL of saline via a nasogastric tube.

Several studies in animals have confirmed the ability of tonometry to provide an early signal of gut ischemia in porcine models of hemorrhagic and septic shock and to indicate loss of ileal mucosal barrier integrity. Clinical investigations in critically ill patients also have documented the value of tonometric $pH_1$ assessment as a means for predicting massive bleeding from stress ulceration, mortality in surgical intensive care unit patients, intraoperative assessment of splanchnic hypoperfusion, and prediction of complications in cardiac surgery patients. In a prospective trial, survival was greater in critically ill patients whose therapy was guided by the $pCO_2$ in samples of gastric fluid.

The implementation of the prior art tonometric techniques, however, requires relatively costly equipment, for example, a special nasogastric tube fitted with a silicone balloon. Furthermore, the relatively large diameter of the prior art equipment also has prevented its use in neonatal and pediatric patients, where alternative means of monitoring perfusion, such as Swan-Ganz catheterization, are impractical and seldom used. Also, the prior art techniques are relatively slow in response, generally precluding real-time monitoring. Also, the prior art techniques generally require transport of extracted samples to an analysis site, resulting in increase in costs due to transport, as well as increase in risk of sample contamination or loss during such handling. Moreover, correction for temperature of the gastrointestinal lumen is also required; the latter is inherently difficult to accomplish in a normal clinical setting.

It is an object of the present invention to provide an improved tonometric method and apparatus for measuring gastrointestinal intraluminal $pCO_2$ and optionally $pO_2$.

Another object is to provide a method and apparatus for continuously monitoring intraluminal gastrointestinal $pCO_2$ and optionally $pO_2$.

Yet another object is to provide a method and apparatus for measuring intraluminal gastrointestinal $pCO_2$ and optionally $pO_2$ in small patients, where size restricts the use of conventional tonometry.

SUMMARY OF THE INVENTION

The present invention is a method and apparatus for measuring or monitoring $pCO_2$ and optionally $pO_2$, on a real-time basis, in the stomach or the intestine using air tonometry with an in situ sensor. The intraluminal measurements are made using a catheter having a $CO_2$ sensor and optionally, an $O_2$ sensor near its distal end for in situ sensing. Instrumentation supporting the sensor may be located within the patient or external to the patient.

In an alternative form, the intraluminal measurements may be made using a catheter having two lumens which are coupled near the distal end of the catheter, with a region of one of the lumens, or the region coupling the lumens, being separated from the region exterior to the catheter by a gas permeable membrane. In the latter form, at the proximal end of the catheter, the lumens are coupled in a manner providing a recirculatory air flow through the lumens, with the distal end positioned at a desired location in a patient, $CO_2$ concentration, and optionally $O_2$ concentration, are measured in the circulating air with an analyzer which is external to the patient.

In the absence of mesenteric ischemia, the invention provides an estimate of the arterial $pCO_2$ and/or $pO_2$, permitting ventilator adjustments without the requirement for blood sampling and blood gas analysis. In the presence of mesenteric ischemia, the invention provides a precise indication of the adequacy of splanchnic perfusion under the conditions of normal and hypercarbia, providing a real-time measure of the status of shock at the end-organ level and of the efficacy of clinical interventions to ameliorate shock. There is no requirement, as in the prior art, for insertion of liquid-filled gas permeable balloons in the gut, followed by long waits for equilibration.

In the preferred form of the invention, the $CO_2$ sensor, and optionally the $O_2$ sensor, and their cable, fiber or telemetering circuitry are embedded in the wall of a tube in order to produce an easily inserted catheter. Preferably, the catheter has a dual purpose, such as air tonometry and decompression/alimentation. There are several catheter locations that are particularly clinically useful: nasogastric, nasoduodenal/nasojejunal, needle jejeunostomy, and colonic. The latter three locations have the advantage of bypassing gastric acidity so that $H_2$ blockage is not required. Other locations may also be of use, particularly in the setting of abdominal surgery where other segments of the intestine are accessible for insertion of the catheter. The duration of placement may be either acute or chronic. An implantable probe may also be left in place indefinitely with the sensor electronics inside or outside of the body. The probe may also be used on an acute basis for the duration of a surgical or other short-term procedure. These examples are illustrative of the invention's usefulness and are not a comprehensive list intended to exclude other potential procedures; they only represent preferred modes.

The $CO_2$ sensor and the optional $O_2$ sensor attached to the catheter, or externally located for the recirculating air embodiments, may monitor changes continuously, log readings, trip alarms, or cause actuators to perform therapeutically or diagnostically indicated functions (e.g. titration of a drug). Utilizing indwelling $CO_2$ and optional $O_2$ sensor equipped catheters (henceforth designated as air tonometers), or the recirculating air embodiments, a clinician can evaluate rapid (e.g. minute to minute) changes in sphlanchnic perfusion and observe the impact of therapeutic interventions, much in the same manner that hemodynamic monitoring is employed. Such air tonometers appear to be more sensitive mid more relevant than prior art pulmonary arterial hemodynamic and oxygen transport indices.

The air tonometry method of the invention is clinically useful insofar as it offers certain advantages over liquid tonometry. Typically, accuracy need only be to one part in ten, since achieving 1% accuracy is probably no more useful clinically than 10%. The method of the invention is several times faster than liquid tonometry. Updates every few minutes may readily be provided, with readings as fast as several per minute. The air tonometry probes of the invention are inexpensive and simple.

Further improvement over the state of the art is the presence of an optional oxygen sensor, which allows cross correlation with the changes in $pCO_2$, permitting confirmation of the implied changes in localized blood flow.

Gas calibration lumens having ports to the sensing region may also be provided in the catheter to further improve the reliability of certain gas sensors, by providing a means of introducing a gas of known concentration to sensing region, allowing calibration of the gas probes.

Various methods of implementing the invention may differ with respect to cost, ease of application, training difficulty, failure modes, and specifics of the patient's condition. For instance, fully self-contained and self-powered air tonometry probes may be appropriate in certain chronic conditions with radio linkage out of the patient. Issues of durability, toxicity, calibration drift, and thermal sensitivity then become paramount. Air tonometry of the invention is relatively insensitive to body temperature ranges in comparison to liquid tonometry, independent of probe construction, since absorbed gas partial pressure decreases rapidly in liquid as temperature increases. Some clinical protocols may advise second or multiple tonometry methods simultaneously for calibration or sensitivity to a variety of gases. A combination catheter/probe may measure the same gas or multiple gases for reasons of mutual calibration, differing sensitivities, or time varying properties. The invention may also be used to measure any gas, in particular, oxygen, and others of clinical interest, with a suitable sensor. If the probe were inadvertently placed in a liquid-filled pocket within the gastrointestinal tract, then the measurements made by the remote sensor would continue to indicate intraluminal $pCO_2$ with accuracy, but with a significantly prolonged equilibration time. More elaborate probe geometries, such as a probe having multiple circumferentially placed membranes, may be used to minimize any such problem.

With the invention, real-time measurement or monitoring of $CO_2$ and/or $O_2$ concentrations in the gut may be obtained with relatively low cost, and small sized-equipment, permitting use in correspondingly small patients, including the very low birth weight infant.

BRIEF DESCRIPTION OF THE DRAWINGS

The foregoing and other objects of the invention, the various features thereof, as well as the invention itself, may be more fully understood from the following description, when read together with the accompanying drawings, in which.

DESCRIPTION OF THE PREFERRED EMBODIMENTS

Figure 1:
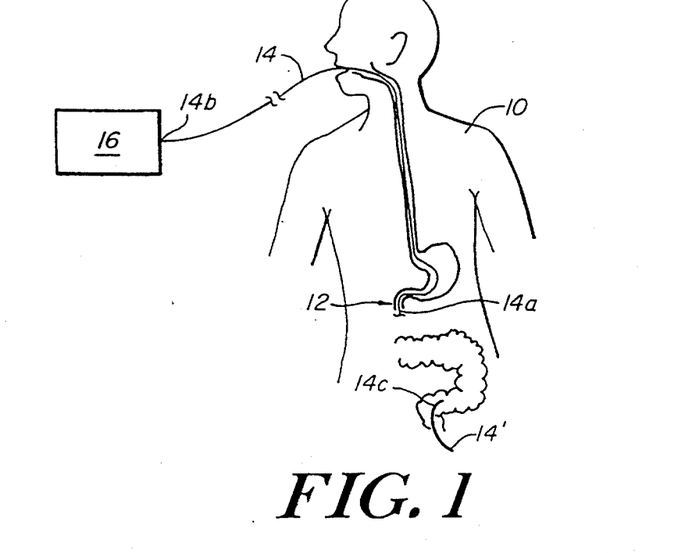
FIG. 1 shows an air tonometery apparatus in accordance with the invention with the apparatus being in place within a patient.

An embodiment of the present invention is shown in FIG. 1. In that figure, a patient 10 is shown with a nasogastric catheter 14 in place for operation in accordance with the invention. The catheter 14 has a distal tip 14a located at a desired intraluminal location in the patient 10. A gas sensor 12 is positioned at the distal tip 14a of the catheter. The catheter 14 has a proximal tip 14b coupled to a $pCO_2$, and optionally $pO_2$, output signal generator and/or recorder 16 external to patient 10. In other forms of the invention, the catheter may, for example, be a nasojejunal or, jejunostomy catheter, where the tip 14a is located in the jejunum. Alternatively, a colonic configuration may be configured where tip 14c of catheter 14 is located in the bowel.

In one form of the invention, the sensor 12 of catheter 14 has a Severinghaus electrode $CO_2$ sensor, positioned at distal tip 14a of the catheter 14, with electrical signal lines extending from the sensor, along the catheter 14, and to an external output signal generator, such as a conventional signal analyzer, such as model DAS-8, manufactured by Kiethly Metrabyte. Alternatively, the sensor may be part of a compact r.f. telemetry package which is affixed to catheter 14. The sensor 12 may also include a conventional $O_2$ sensor.

Figure 2:
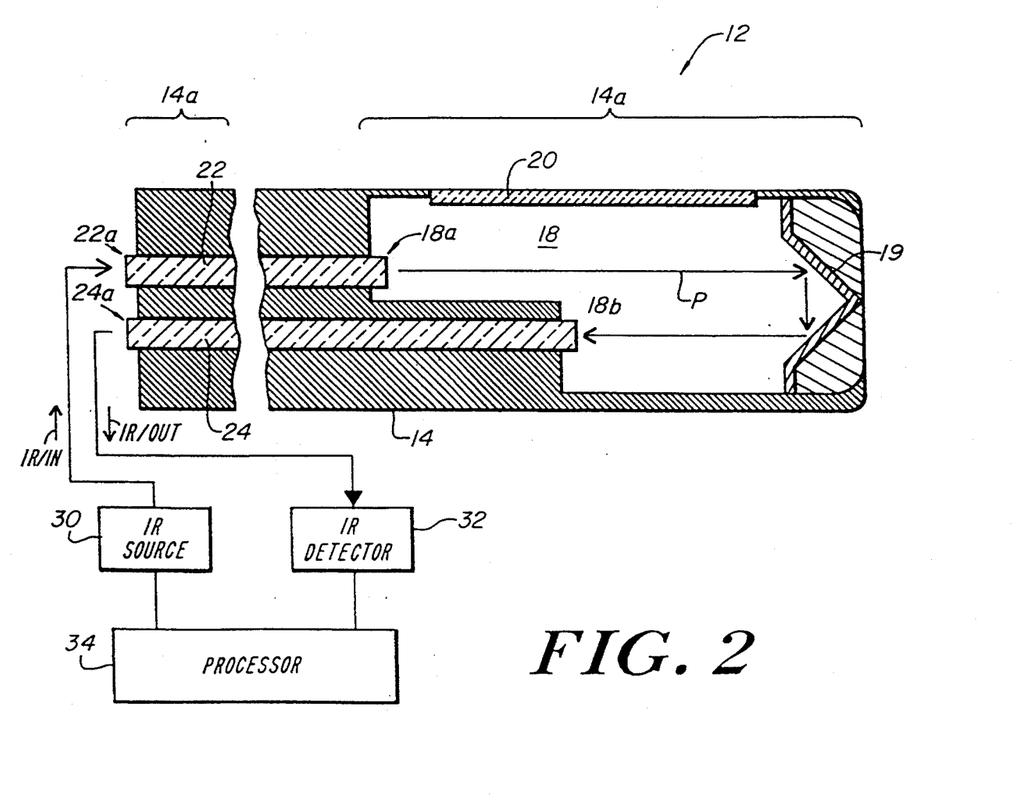
FIGS. 2-4 show, partially in block diagram and partially in schematic form, alternative embodiments of the invention.

In another form, as illustrated in FIG. 2, the catheter 14 may be solid, i.e. no lumens, and define a open-faced region 18 near its distal tip 14a, where the open face of that region 18 is spanned by a gas permeable membrane 20, to establish a closed gas sensing region coextensive with region 18. A first infrared (IR) light transmissive optical fiber 22 extends from a point 18a at the boundary of region 18, along catheter 14, to a point 22a near the proximal end 14b of catheter 14. A second infrared light transmissive fiber 24 extends from a point 18b at the boundary of region 18 along the light path of point 18a, along catheter 14, to a point 24a near the proximal end 14b of catheter 14.

Figure 4:
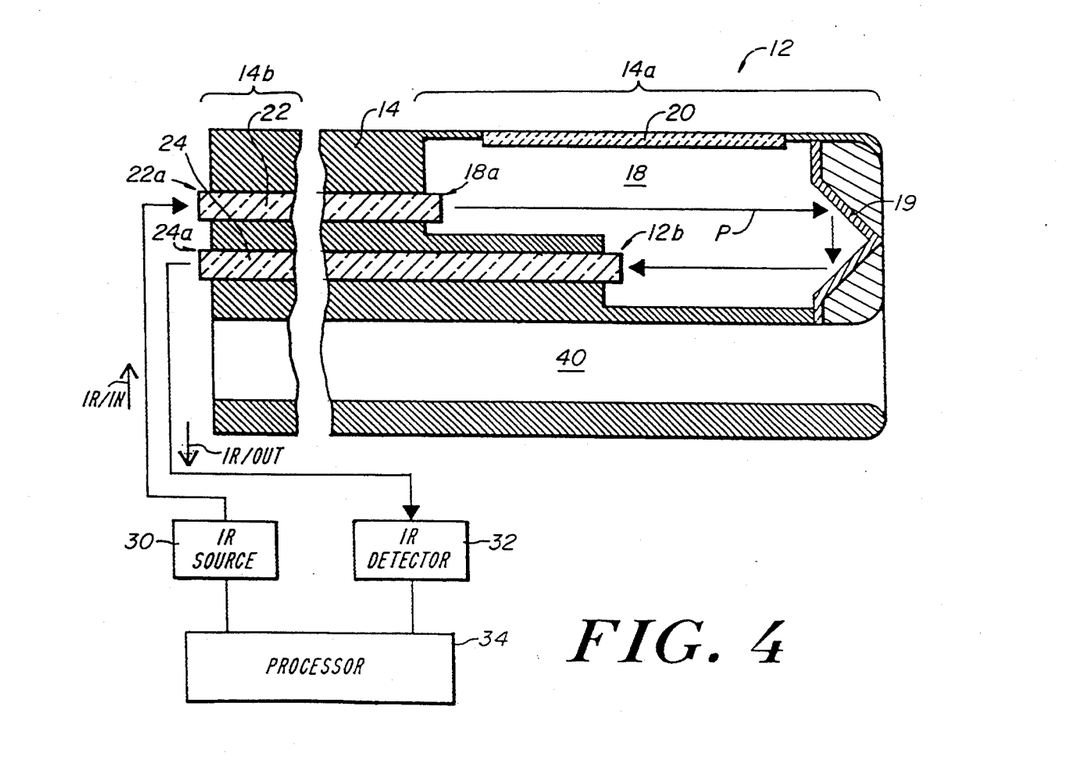

In the illustrated embodiment of FIG. 4, the membrane 20 is only on one side of the catheter, but in other embodiments the catheter may include multiple membranes in different circumferential locations. In the latter form, even if the distal tip is pressed against the gut wall, only one membrane would be blocked, while at least one other membrane would permit gas permeation into region 18.

A reflector 19 is positioned within region 18 at the distant end of that character so that the fibers 22 and 24 are optically coupled along a path P. In other forms of the invention, different reflector configurations may be used, and, in some forms, the fiber ends may be opposite each other so that no reflector is necessary to optically couple the fibers.

The proximal end of fiber 22 is coupled to an infrared (IR) source 30, and the proximal end of fiber 24 is coupled to an infrared (IR) detector 32. Source 30 and detector 32 are coupled to a processor 34, which may be, for example, a programmed digital computer with an analog-to-digital converter at its input.

With this configuration, the catheter is placed so the distal tip 14a is positioned at a desired intraluminal location in the gut, thereby defining the adjacent local region of the intragastrointestinal lumen as the region-of-interest for which measurements are to be made. The processor may selectively actuate source 30 to direct IR radiation along fiber 22 toward region 18. A portion of that IR radiation propagates across region 18 and is transmitted along fiber 24 to detector 32, where a signal representative of the received radiation is generated and transferred to processor 34. Processor 34 is adapted, using conventional techniques, to measure the intensity of the received radiation and to provide an output signal representative of the concentration of $CO_2$ in the region 18, which is at equilibrium with the intraluminal region of the gut adjacent to that region 18. The latter signal corresponds to the intraluminal gastrointestinal $pCO_2$ and thereby provides an estimate of the mucosal gas tension. Multiple optical frequencies can be used for the detection of multiple gases and the calibration of the optical sensor and light path. These different optical frequency signals may be transmitted simultaneously or sequentially to optimize detection.

Figure 3:
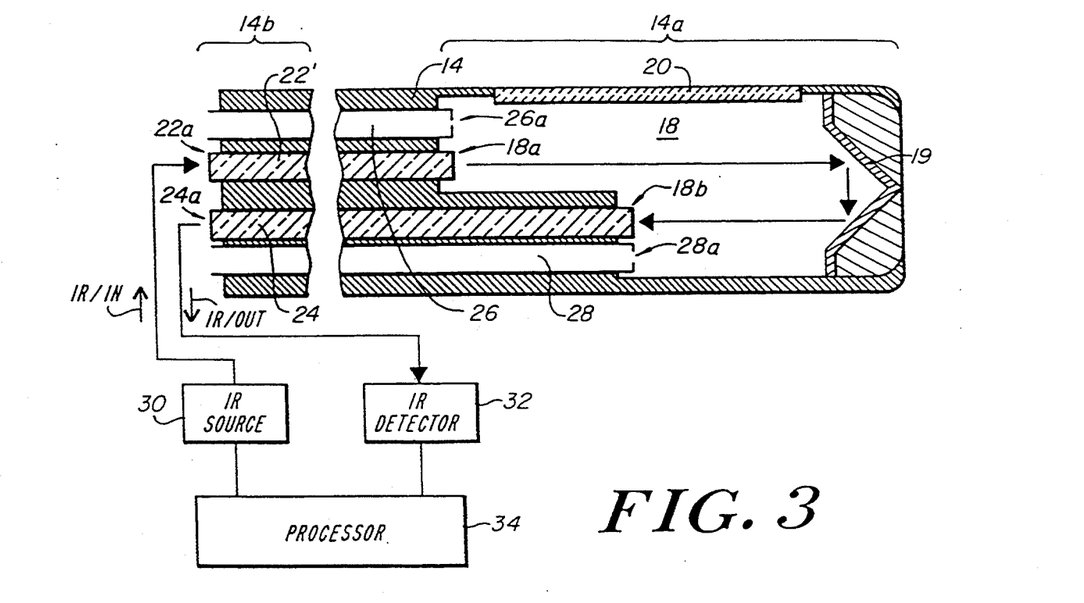

In various other forms of the invention, for example, as shown in FIG. 3, the catheter 14 may include two calibration lumens 26 and 28 which extend from end 14a to end 14b. With this configuration, the $CO_2$ sensor may be calibrated in situ by establishing a known $CO_2$ concentration in region 18, prior to equilibration of that chamber with the gastrointestinal tract. The gas calibration lumens 26 and 28 communicate with the gas sample chamber 18 via small gas calibration ports 26a and 28a, respectively. These calibration lumens are sealed during normal measurements, for example by valves either within the catheter, or external to the catheter. When a small fixed amount of gas at known concentrations (e.g. room air) is injected through the input calibration lumen 26, through the gas sample chamber 18, exiting through the output calibration lumen 28, a known standard is provided to the gas sensors for calibration.

Figure 5:
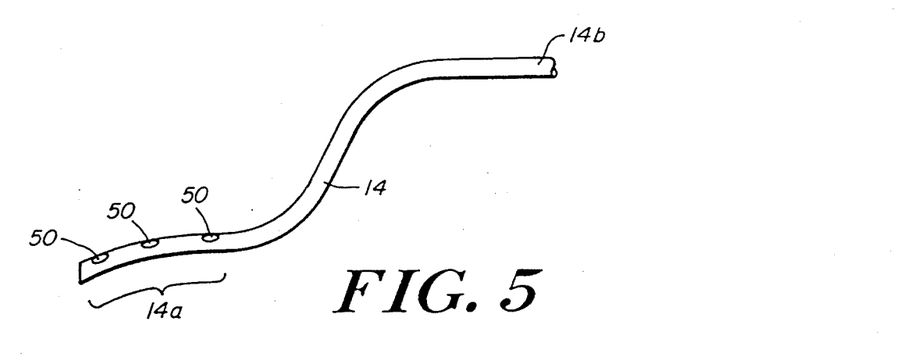
FIG. 5 shows, in section, a multiple sensor configuration of the invention.

Another form of the invention, for example, as shown in FIG. 4, the catheter 14 may include one or more lumens (40) extending between the distal and proximal tips, for use in other functions. The sensor may be configured with other arrangements for sensing $CO_2$ and optionally $pO_2$, which provide measures of $CO_2$ and optionally $pO_2$ concentration adjacent thereto. In various other forms, such as that shown in FIG. 5, one or more gas sensors 50 may be placed at desired locations along the catheter, so that partial pressures may be measured or monitored at corresponding locations in the gut simultaneously, as desired. The locations of the various sensors along catheter 14 are considered to be "near" the distal end 14a of the catheter even though they are not immediately adjacent to the distal tip.

Figure 6:
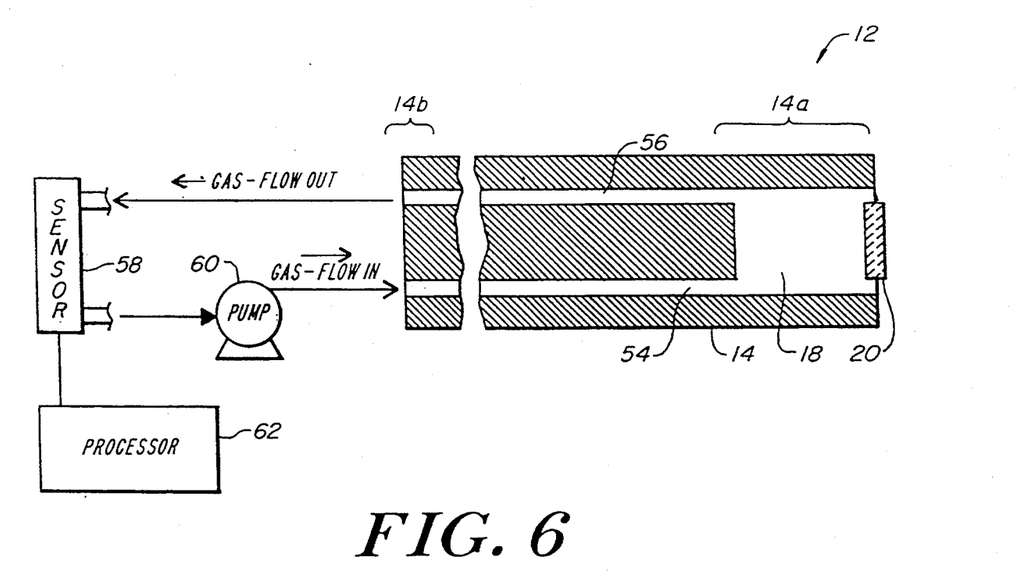
FIGS. 6-8 show, partially in block diagram and partially in schematic form, alternative embodiments of the invention.

In yet other forms of the invention, such as that shown in FIG. 6, the sensor region 18 of catheter 14 may be coupled by lumens 54 and 56 to an external detector 58, with a pump 60 establishing a fixed quantity of continuously circulating air through lumen 54, chamber 18, and lumen 56 to $CO_2$ (and optionally $O_2$) sensor 58. The air passing through chamber 18 communicates with the gastrointestinal lumen through membrane 20. A processor 62 is coupled to $CO_2$ sensor (and optionally $O_2$) 58, and provides an output signal representative of the $CO_2$ (and optionally $O_2$) concentration in the sensor region 18. This form of the invention is particularly useful when small size is important because a very small diameter catheter may be used with all instrumentation outside the patient.

Other forms of the invention may incorporate fluorescent, chemical, photometric, spectrophotometric, phosphorescent, chemiluminescent, paramagnetic, polarographic, and chemical sensitive transistor gas sensors for the determination of $CO_2$, $O_2$ and other gases. Several examples of commonly known technologies for implementing these sensor designs are listed in Table 1.

TABLE 1

| Property | Gas | Technology | Reference |
|---|---|---|---|
| Chemiluminescence | $O_2$ | TMAE | 7 |
| Fluorescence | $O_2$ | Halide/Ag/fluorescein | 7 |
| Chemical/Optical | $CO_2$ | Phenol Red | 10 |
| Chemical | $CO_2$ | pH in buffered solution | 9 |
| Spectrophotometric | $O_2$ | pyrene butyric acid | 4 |
| Spectrophotometric | $CO_2$ | IR absorption | 1 |
| Polarographic | $O_2$ | Clark electrode | 2 |
| Paramagnetic | $O_2$ | Effect on density | 5,6 |
| Chemosensor | $CO_2$ | ISFET | 3 |

The references set forth in Table 1 are:

1. Bullock B. W., Silverman S., (1950) A Rapid Scanning Spectrometer for Oscillographic Presentation in the Near Infra-Red, *J. Opt. Soc. Am.*, 40(9):608–615

2. Clark, L. C. (1956) Monitor and control of blood and tissue oxygen tension. *Trans. Am. Soc. Artif. Intern. Organs*, 2:41–48

3. Kohama, A., Nakamura, Y1, Nakamura, M., et al.: Continuos monitoring of arterial and tissue $pCO_2$ with sensors based on the pH-ISFET. *Crit. Care Med.,* 12:940,1984

4. Lubbers, D. W., Optiz N. (1976) Quantitative fluorescence photometry with biological fluids and gases. *Adv. Exp. Med. Biol.,* 75:65–69

5. Pauling, L Wood, R. E. Sturdevant, L. H. (1949) An instrument for determining the partial pressure of oxygen in a gas., *Science* 103:338

6. Rein H. (1944) Magnetsche 02 Analyze in Gasgemischen. *Pfleger Arch. Gesamte Physiol.* 247:576–592

7. Seitz, R. W. (1984) Chemical sensors based on fiber optics. *Analytical Chemistry,* 56(1)16A–34A 8. Severinghaus, J. W., Bradley A. F. (1958) Electrodes for blood pO2 and pCO2 determination *J. Appl. Physiol.* 13:515–520

9. Stowe R. W., Randall, B. F. (1954) Rapid measurement of the tension of carbon dioxide in blood. *Arch. Phys. Med. Rehabil.,* 38:656–650

10. Vurek G. G., Feustel P. J., Severinghaus J. W., (1984) A fiber optic pCO2 sensor. *Ann. Biomed. Eng.,* 11:499–510

Figure 7:
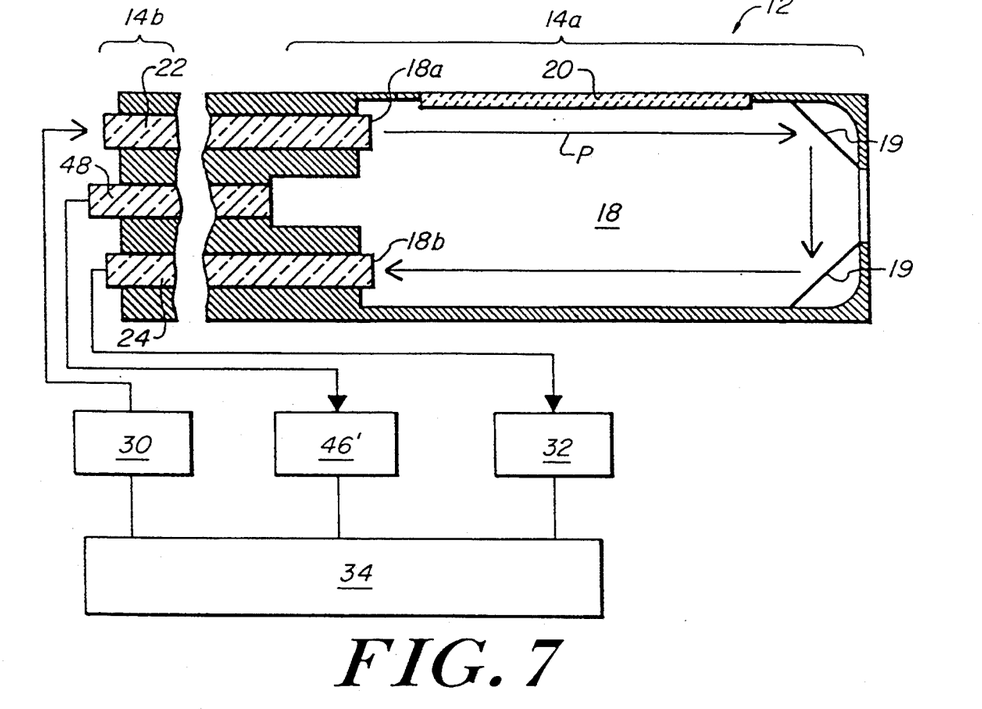

FIG. 7 is illustrative of a dual measurement device, similar to the device of FIG. 2 but where a chemiluminescent oxygen detector 46' is also included, allowing a direct reading of an oxygen sensitive chemical such as TMAE (dimethylaminoethylene) in the chamber 18. In this case, steady state chemiluminescence is directly proportional to the quantity of oxygen diffusing into the material and can be read with a single optical fiber 48 extending along the central axis of catheter 14 back to detector 46. This embodiment can be combined with the optional gas calibration ports or optional auxiliary lumens to provide several configurations of the catheter depending on need.

Figure 8:
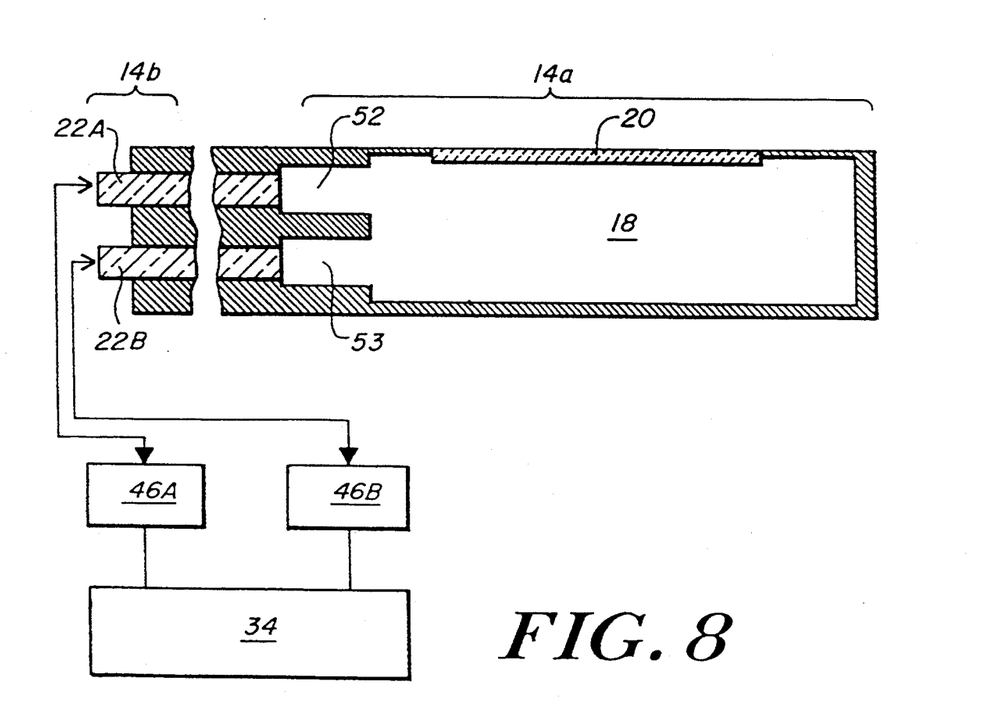

The invention may also be embodied with a fluorescent or phosphorescent sensor which operates on a similar principle, as illustrated in FIG. 8, a catheter 14 is coupled to two separate optical emitter/detectors 46a and 46b and associated optical fibers 22A and 22B, respectively. The single optical fibers 22A and 22B first carry an excitatory optical signal to gas sensitive material in region 18. The gas sensitive material, which preferably is immobilized in regions 52 and 53, then fluoresces or phosphoresces based on the proportions of the excitatory optical signal and the local gas concentration, to which the chemical is sensitive. The same fibers 22A and 22B may be used with emitter/detectors 46a and 46b respectively, to then read the resulting optical signal given off by the fluorescent or phosphorescent material as a means of measuring the local gas concentration of interest. Gray et. al., (U.S. Pat. No. 5,176,882) describe a similar technique for multiple gas measurements in blood by doping a polymer with multiple sensitive fluorescent dyes, interpreting each dye at their characteristic wavelengths.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method for measuring partial pressure of one or more gases in the gastrointestinal lumen of a patient comprising the steps of:

A. defining an intraluminal region as a region-of-interest within the gut of a patient by inserting a catheter into said patient, said catheter having a distal end and a proximal end, whereby said distal tip is located in a desired intraluminal region in the gut of said patient and said proximal end is external to said patient, and wherein said catheter further includes an open-faced chamber defined near the distal end of said catheter, and a gas permeable membrane spanning said open-faced chamber to define a closed gas-filled gas sensing region therein, said closed gas sensing region having substantially no fluidic communication with said proximal end, and includes a detector, said detector including a $CO_2$ sensor affixed to said catheter near said distal end and including selectively operative sensor means for generating at said proximal end a signal representative of the concentration of $CO_2$ in said intraluminal region adjacent to said distal end, B. sensing in said gut the concentration of said gases in said region-of-interest, and C. generating a signal representative of said concentration, said signal being representative of the partial pressure of said gases in said region-of-interest, wherein said sensing step and said generating step include the step of operating said sensor means.

2. The method of claim 1 wherein said gases include one or more gases selected from the group consisting of carbon dioxide ($CO_2$) and oxygen ($O_2$).

3. The method of claim 2 wherein the number of gases measured is greater than 1, and wherein said method includes the step of sensing in said gut the partial pressure of said gases with separate sensors.

4. The method of claim 1 wherein said detector further includes an $O_2$ sensor affixed to said catheter near said distal end and including selectively operative sensor means for generating at said proximal end a signal representative of the concentration of $O_2$ in said intraluminal region adjacent to said distal end, and wherein said sensing step and said generating step include the step of operating said sensor means.

5. An intraluminal gastrointestinal gas measuring system, comprising:

A. an elongated catheter having a distal end and a proximal end,

B. one or more gas sensors affixed to said catheter near said distal end, wherein at least one of said gas sensors includes an open-faced chamber defined near the distal end of said catheter, and a gas permeable membrane spanning said open-faced chamber to define a closed gas-filled gas sensing region therein, said closed gas sensing region having substantially no fluidic communication with said proximal end, and wherein at least one of said gas sensors is adjacent to said closed gas sensing region and in optical communication with said proximal end, and C. sensor means for generating at said proximal end a signal representative of the partial pressure of said gases external to said catheter and adjacent to said gas sensors.

6. A measuring system according to claim 5 wherein at least one of said sensors is a $CO_2$ sensor.

7. A measuring system according to claim 6 wherein at least one of said sensors is an $O_2$ sensor.

8. A measuring system according to claim 6 wherein said sensor means is selectively operative and includes:

A. a first optically transmissive optical fiber extending from a first point at the boundary of said gas sensing region to said proximal end, B. a second optically transmissive optical fiber extending from a second point at the boundary of said gas sensing region to said proximal end, said first optical fiber at said first point being optically coupled to said second optical fiber at said second point, C. means for directing optical radiation through said first fiber from a point near said proximal end toward said gas sensing region, and D. means for detecting at a point near said proximal end optical radiation coupled from said first fiber across said gas sensing region to said second fiber and through said second fiber.

9. A system according to claim 8 wherein said sensor means further comprises means coupled to said second fiber near said proximal end for determining gas concentration in said gas sensing region from said detected optical radiation.

10. A measuring system according to claim 9 wherein said catheter further comprises A. first calibration lumen extending from said proximal end to and in selective communication with said chamber of said sensor, B. second calibration lumen extending from said proximal end to and, in selective communication with said chamber of said sensor, C. means for selectively passing a calibration gas through said first calibration lumen and said chamber to said second calibration lumen, and D. means for operating said sensor means while said calibration means is passing said calibration gas through said sensing region.

11. A measuring system according to claim 9 wherein said catheter further includes at least one open ended lumen extending between said distal end and said proximal end.

12. A measuring system according to claim 5 wherein said catheter further includes at least one open ended lumen extending between said distal end and said proximal end.

13. An intraluminal gastrointestinal gas measuring system, comprising:

A. an elongated catheter having a distal end and a proximal end, and having:
  i. an open-faced chamber near said distal end and a gas permeable membrane spanning said chamber to define a gas-filled gas sensing region,
  ii. a first lumen extending from said proximal end to said sensing region, and
  iii. a second lumen extending from said proximal end to said gas sensing region B. means as for coupling said first and second lumens at said proximal end to establish a closed gas flow path through said first and second lumens and said gas sensing regions, C. flow means for establishing a continuously recirculating flow of gas in said gas flow path, and D. detector means for determining the gas concentration in said gas flow path.

14. A system according to claim 13 wherein said detector means includes means for determining $CO_2$ concentration in said gas flow path.

15. A system according to claim 13 wherein said detector means includes means for determining $O_2$ concentration in said flow path.

16. A system according to claim 13 wherein said catheter further includes at least one open ended lumen extending between said distal end and said proximal end.

* * * * *